United States Patent [19]

Shaw et al.

[11] Patent Number: 4,857,331

[45] Date of Patent: Aug. 15, 1989

[54] SUGARLESS PECTIN DELIVERY SYSTEM

[75] Inventors: James J. Shaw, Morristown; Frank J. Bunick, Budd Lake, both of N.J.

[73] Assignee: Warner-Lambert Company, Morris Plains, N.J.

[21] Appl. No.: 175,818

[22] Filed: Mar. 31, 1988

[51] Int. Cl.[4] ............................................... A61K 9/68
[52] U.S. Cl. ................................. 424/440; 424/439; 424/441; 424/484; 424/485; 424/488; 426/517
[58] Field of Search .................. 424/439, 195.1, 440, 424/441

[56] References Cited

U.S. PATENT DOCUMENTS

| | | | |
|---|---|---|---|
| 4,511,561 | 4/1985 | Madaus et al. | 424/195.1 |
| 4,551,331 | 11/1985 | Rudin | 424/195.1 |
| 4,565,702 | 1/1986 | Morley et al. | 426/93 |
| 4,689,229 | 8/1987 | Banik | 424/195.1 |
| 4,766,004 | 8/1988 | Moskowitz | 424/439 |

OTHER PUBLICATIONS

*Hawley's Condensed Chemical Dictionary*, eleventh ed., selected sections (1987).
Kelco, "Algin/Hydrophilic Derivatives of Alginic Acid for Scientific Water Control", second ed., p. 6–8.
*Remington's Pharmaceutical Sciences*, fifteenth ed., selected sections (1975).
*Sprowls' American Pharmacy*, seventh ed., selected sections (1974).
Toft, K., "Interactions Between Pectins and Alginates", *Prop. Pd., Nutr. Sci.*, vol. 6, pp. 89–96 (1982).

*Primary Examiner*—Thurman K. Page
*Assistant Examiner*—Penny Prater
*Attorney, Agent, or Firm*—Sandra G. Field

[57] ABSTRACT

A sugarless ingestible gel confectionary delivery system which includes a pectin gel component, an algin gel component and a polymer network gel component in amounts sufficient to form a gel confectionery unit. The inventive gel confectionery unit has reduced intrinsic viscosity prior to gelation which permits the inclusion of an edible insoluble solid in an amount sufficient to strengthen the internal combination pectin-algin gel network and to bind internal moisture sufficiently to enhance mold removal capabilities. The delivery system also includes hydrogenated starch hydrolysates. The delivery system may also include a further active ingredient such as a drug, medicament, or nutritional supplement. The product and method of the present invention also includes a composition in which the gel delivery system can be molded directly in the receptacle which is used to dispense the confectionery unit to the consumer.

37 Claims, 3 Drawing Sheets

SUGARLESS PECTIN DELIVERY SYSTEM

FIELD OF THE INVENTION

This invention relates to a sugarless pectin delivery system and a method of preparation thereof. More particularly, this invention relates to a sugarless confectionery delivery system which includes a pectin gel component, an algin gel component and a polymer network gel component in amounts sufficient to form a gel confectionery unit. The inventive gel confectionery unit as thus prepared has reduced intrinsic viscosity prior to gelation which permits the addition of an edible insoluble solid in an amount sufficient to strengthen the internal pectin-algin gel network and to bind internal moisture sufficiently to enhance mold removal capabilities. The delivery system also includes hydrogenated starch hydrolysates. This invention also relates to the lowering of the intrinsic viscosity of a sugarless pectin system which allows the sugarless system to be cooled and deposited into molds at a solids level which is comparable to the solids level in the finished sugarless delivery system unit. The delivery system of the invention may also include a further active component, such as a drug or medicament, especially a laxative. Thus, products prepared in accordance with this invention can provide a high percentage of added solid material, such as drugs, nutritional supplements and the like, in an organoleptically-acceptable sugarless soft gel confectionery structure.

BACKGROUND OF THE INVENTION

Prescribed daily dosage amounts of fiber are often high, such that the patient must administer the fiber or fiber composition several times per day. Numerous fiber-containing products are available in the market in the form of breakfast cereals, laxative beverages, bran tablets and cereal bars. While the health benefits of fiber consumption are now well known to the general public, and the public has accepted the desirability of increased fiber consumption, the unpleasant fibrous mouthfeel and texture of the currently available fiber-containing products has resulted in dosage compliance problems.

Many fiber markets have experienced consumer reluctance to eat sufficient amounts of fiber to provide therapeutic benefits because of the generally objectionable taste of the fiber or the high caloric content associated with masking the objectionable taste. The dry, unpalatable texture and mouthfeel of fiber often requires the incorporation of fats and carbohydrates (masking agents) in amounts which effectively dilute the fiber dosage per unit of product and substantially increase the caloric content of the product.

Commercially available confectionery products containing fiber are generally of the granola-type. Chocolate, fruits and nuts are often added with other confectionery ingredients to enhance the palatability of the final product. Snack meals consisting of granola-type bars and cookies have become increasingly popular among health-conscious consumers as a substitute for traditional meals. Although these forms of fiber-containing products are generally more pleasant tasting, they typically do not deliver the high concentration of fiber necessary to achieve optimum dosage. Moreover, inasmuch as these products have a high sugar content (typically up to about 70% added sugars), they are contrary to the health conscious consumer's desire to avoid refined sugars, as well as those persons, such as diabetics, who must also avoid and/or restrict their intake of sugars and sugar-containing products.

Inadequate patient compliance with prescribed drug therapies is another problem, particularly when the drug has an unpleasant taste, after-taste or gritty mouthfeel. Drugs such as phenolphthalein, dextromethorphan, danthron, sennosides, cholestyramine and potassium chloride are known to taste unpleasant. The prior art has disclosed products to mask the taste of these drugs, but the products themselves often suffer from their own unpleasant tastes or texture.

The overall trend, therefore, in patient use of the prior art products containing fiber or drugs, has been to deviate from the prescribed dosage or frequency of dosage, thereby diminishing the effectiveness of the therapy.

In a related disclosure, U.S. Pat. No. 4,698,232 to Sheu et al., a unique confectionery form for delivering fiber is provided which includes elements of nougat technology, boiled candy technology and coating technology, to achieve an acceptable composition containing about 20% to 30% dietary fiber. The solution provided in the above-referenced patent is excellent if the consumer finds the foam-type matrix described therein desirable.

In another related disclosure, U.S. application Ser. No. 032,840, filed Mar. 31, 1987, a unique sugar-containing pectin gel delivery system is provided which includes a pectin gel component in an amount sufficient to form a gel confectionery unit and an edible insoluble solid. This delivery system is a viable and pleasant alternative for consumers seeking to increase their intake of dietary fiber who enjoy a gel-type matrix. This delivery system includes the use of sugar, such as sucrose, and corn syrup and, accordingly, is not suitable for consumers seeking to avoid sugar by consuming sugarless products. Moreover, it was found that the direct replacement of hydrogenated starch hydrolysates for the sucrose/corn syrup components of the sugar pectin gel did not yield an acceptable sugarless pectin gel delivery system product. Direct replacement resulted in a confectionery gel product having a higher than suitable water activity which rendered the product unstable with respect to microbial activity. Merely decreasing the water content of the direct replacement sugarless pectin gel in an attempt to avoid this problem caused additional problems. There was a significant increase in the depositing viscosity of the delivery system, thereby rendering the molten mix not flowable for deposition into the mold cavities, and a tougher, more rubbery textured final product. Accordingly, direct replacement of hydrogenated starch hydrolysates for the sugar/corn syrup component of the prior art resulted in a variety of completely different problems and a commercially unusable product.

Two patents which disclose palatable drug formulations use coacervation techniques to combine cholestyramine with modified celluloses. U.S. Pat. No. 3,947,272 shows oral palatable formulations containing aqueous media and cholestyramine. A method of treating hypercholesterolemia is claimed. Chewable products containing cellulosic/gum colloids are disclosed.

U.K. Pat. No. 1,446,352 concerns palatable compositions useful for the treatment of hypercholesterolemia and biliary cirrhosis. The invention provides a liquid composition containing "coacervate of cholestyramine with a cellulose hydrocolloid" derivative. By the term "coacervate" is meant the coagulation of two hydrophilic substances of opposite charge. Representative hydrocolloids are methyl cellulose, sodium carboxymethyl cellulose, hydroxyethyl cellulose and hydroxypropyl cellulose. A water-insoluble dispersing agent, e.g., a substituted carboxymethyl starch, is optional. In making the composition, 1 part by weight of hydrocolloid is combined with 4 to 10 parts of cholestyramine by dry mixing and passing through a No. 80 U.S. standard mesh screen. The resulting powder is then mixed with a liquid to form a coacervate which can be orally administered.

In another related disclosure, U.S. application Ser. No. 698,511, filed Feb. 5, 1985, problems associated with organoleptic acceptability of fiber and drugs are remedied by formation of an aggregate having a particle size of about 4 to about 70 standard mesh. The aggregate includes a substantially anhydrous pre-swelled hydrocolloid and a substrate. Unpleasant taste and undesirable mouthfeel of fiber and/or drug is effectively masked and substantial hydration is delayed until the composition passes through the oral cavity.

It is well-known and generally accepted that the pectin-type gel system possesses premium, preferred organoleptic qualities, that is, these gels have a most tender and desirable chew character. However, although gel systems might provide an acceptable alternative delivery system, several features of gel manufacturing technology and characteristics of the resultant product discourage the use of an otherwise appealing delivery system. For example, normal gel production requires several steps generally including cooking or concentrating, depositing or molding, drying or stoving, removal from starch molds, cleaning of the product, sieving and drying the mold material, and sugar sanding, sugar crystallizing or glazing of the final product. Stoving is the process whereby deposited gels and other similar products lose moisture to obtain their desired final solids content (inverse of the moisture content) because these products would typically be to viscous to deposit if concentrated to their desired final solids content prior to deposition. In addition, uniform distribution of the active throughout the gel product may require addition of the active before cooking or addition of the active while the cooked gel is still in the molten state. Cooking will cause heat-sensitive actives to undergo thermal and/or hydrolytic degradation. Thus, from a production standpoint, a gel dosage delivery system is considered much too labor-, equipment-, time-, and energy-intensive. Furthermore, it is well known that many gels resist compete dissolution in an aqueous environment and little, if any, control can be provided to the release of a unit dosage of active ingredient from the gel.

It has now been discovered, however, that the drawbacks generally occasioned by inclusion of fiber and drugs into gel-type systems are significantly reduced and, in some cases, completely obviated by providing a gel delivery system which utilizes the natural aqueous environment of the oral cavity to mask and accelerate passage of the dissolved active ingredients during ingestion. Furthermore, the problems associated with the laborious process for preparing a suitable gel product have been overcome. In addition, the problems encountered by the direct replacement of hydrogenated starch hydrolysate for the sucrose/corn syrup component of the sugar pectin gel delivery systems have now been overcome. Thus, a sugarless pectin gel-like confectionery delivery system having a desirable chew character is now achievable.

SUMMARY OF THE INVENTION

Figure 1:
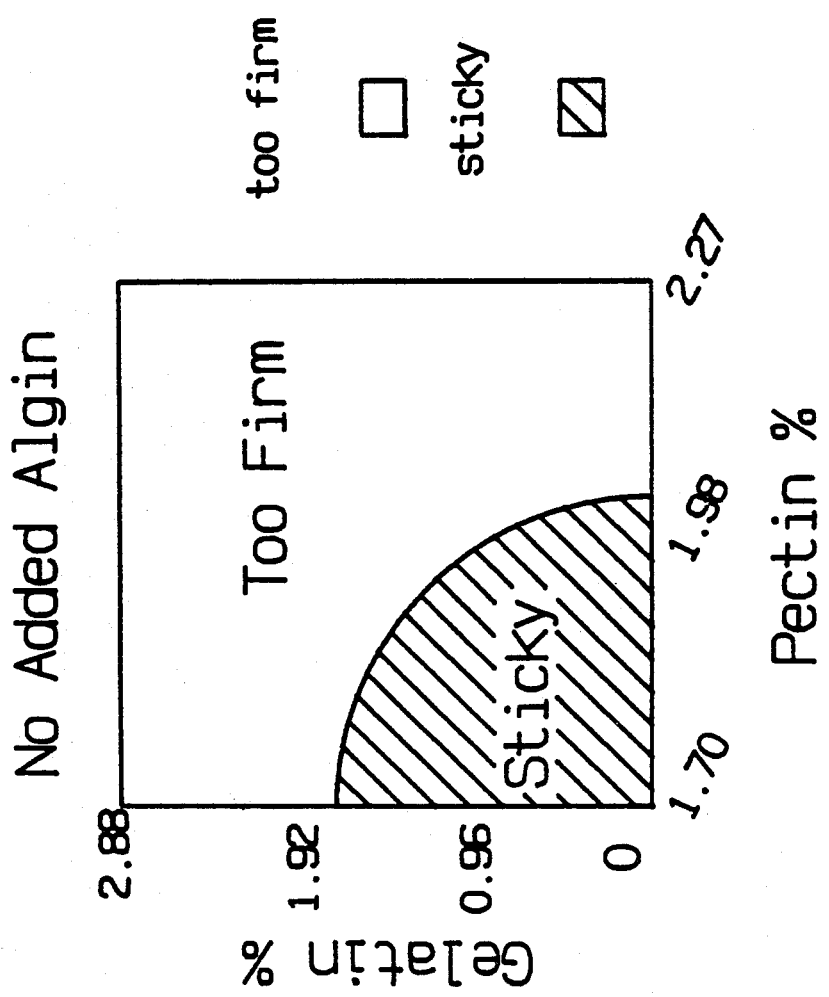
FIG. 1 depicts a slice of a comparative tri-axial graph diagram of gel product properties using varying concentrations of pectin and gelatin without algin.

The present invention includes a sugarless pectin delivery system and a method of preparation thereof which includes a pectin gel component, an algin gel component and a polymer network gel component in amounts sufficient to form a gel confectionery unit. The inventive gel confectionery unit as thus prepared has reduced intrinsic viscosity prior to gelation which permits the addition of an edible insoluble solid in an amount sufficient to strengthen the internal pectin-algin gel network and to bind internal moisture sufficiently to enhance mold removal capabilities. The delivery system also includes hydrogenated starch hydrolysates. Preferably, the delivery system of the present invention also includes a further active component such as drug or medicament, especially a laxative such as phenolphthalein, sennosides and danthron.

The insoluble solid can be selected from one of celluloses, gums, grains, seeds, seed husks, fruits, and mixtures thereof. The inclusion of dehydrated fruits in flake and powder form has been found to be especially effective. Furthermore, the present invention can include the use of a humectant such as glycerin or propylene glycol and the like to enhance control and inclusion of additional solids.

Usually, products made with the present delivery system include pectin in an amount of from about 1% to about 5%, preferably from about 1% to about 3%, and most preferably from about 1.5% to about 2.25% by weight of the final delivery system product. Algin is included in an amount of from about 0.2% to about 1.5%, preferably from about 0.5% to about 1.0%, and most preferably from about 0.6% to about 0.8% by weight. The products in accordance with the present invention can include a total pectin-algin combination of up to about 5.5% of the final delivery system product. The polymer network gel component can be included in an amount of up to about 5%, preferably up to about 3%, and most preferably from about 0.5% to about 2% by weight of the final delivery system product.

The amount of insoluble solid which can be included ranges from about 0.5% to about 20%, preferably from about 4.0% to about 12.0%, and most preferably from about 4.0% to about 10.0% by weight of the final delivery system product. When a laxative is used as the active ingredient in the present invention, the amount included can be from about 0.4% to about 2.5%, and is preferably from about 1.0% to about 2.0% by weight of the final delivery system product.

A hydrogenated starch hydrolysate, or mixtures thereof such as Lycasine ® a commercially available product manufactured by Roquette Freres of France, or Hysta® a commercially available product manufactured by Lonza Inc. of Fair Lawn, N.J., is included in an amount from about 40.0% to about 85.0% (solids basis), preferably from about 50% to about 75%, and most preferably from about 65% to about 75% by weight of the final delivery system product.

The addition of polymer network gel formers such as gelatin, or the combination of glycerin and gelatin, can increase the working time prior to solidification. Increased working time allows better homogeneity to be achieved when large quantities of ingredients are to be added. The addition of algin to a pectin gel causes a decrease of intrinsic viscosity of the pectin prior to gelation along with some reduction in the chewiness of the final product. The inclusion of a polymer network gel former agent offsets this reduced chewiness. The inclusion of the polymer network gel former agent also allows incorporation of greater quantities of insoluble solids, provides binding structure to the total gel system, enhances the chewy texture of the final product, and supplies synergistic film-forming properties, i.e. "skinning," which results in reduced "stickiness" of the final delivery system product. Structural integrity of the gel is thus increased through the addition of gelatin or gelatin and glycerin, notwithstanding the disruption of the gel's structural continuity through the addition of high amounts of insoluble solids.

The algin component can be a sodium alginate or other soluble algin prepared from a variety of natural kelp such as *Macrocystis pyrifera, Ascophyllum nodosum, Laminaria digitata, Laminaria hyperborea* (stipes), and *Ecklonia cava* and *Eisenia bicyclis*, each of which contains varying amounts of mannuronic and guluronic acids and polymer segments. The ratios of mannuronic to guluronic acid content of these kelps and the alginic acids obtained therefrom range from about 31% to about 65% to mannuronic acid and from about 35% to about 69% guluronic acid. The polymer segments include polymannuronic acid segments, polyguluronic acid segments and alternating segments.

As a result of the present invention, several important advantages are obtained. A sugarless, organoleptically-acceptable confectionery gel delivery system has been obtained for consumers who are conscious of the sugar content in their daily intake and desirous of reducing or eliminating such sugars. In addition, the necessity of stoving the gel to remove its excess moisture can be reduced or practically eliminated. Gelation is initiated by adjusting the pH of the molten delivery system having a desirable increased solids content to the proper range. In addition, the molten delivery system has a sufficiently low viscosity to allow the inclusion of greater amounts of insoluble solids. Moreover, significant amounts of active ingredients such as drugs, fibers, and nutritional supplements can be incorporated without destroying the pleasant tasting chewable pectin-algin matrix. Furthermore, since stoving can be eliminated, thermal and/or hydrolytic deterioration of the active ingredient from this source of heat can also be avoided.

Unlike some other gels such as calcium alginate or xanthan gum-locust bean gum, the inventive combination pectin-algin gels disclosed herein dissolve relatively quickly and completely in an aqueous environment to assure a release of the active ingredient upon ingestion. Furthermore, the short chewing texture and lubricity of the masticated particles permits the pectin-algin based vehicle to be easily swallowed. Thus, the texture enhances the minimization of the contact between the mouth taste sensors and potentially unpalatable active ingredients. This factor becomes very significant when the active ingredient being delivered is gritty in texture, such as dietary fiber and cholestryamine.

Moreover, pectin-algin gels deliver a degree of satiety when consumed. They also have the desirable physiological property of blood sugar moderation. Furthermore, the dosage form is easy to chew and is therefore desirable for geriatric use. Additionally, product tampering can be detected in view of the primarily non-reversible nature of the valence pectin-algin gel system.

For a better understanding of the present invention, together with other and further objects reference is made to the following description, and its scope will be pointed out in the appended claims.

DETAILED DESCRIPTION OF THE INVENTION

Generally, this invention involves a mixed hydrocolloid system. More particularly, the invention involves the use of an algin gel component and optionally a polymer network gel component to permit the addition of insoluble solids to a sugarless pectin gel system to result in a product which can be conveniently consumed as a dosage unit. The sugarless pectin gel product has, as a result of the inclusion of the algin and polymer network gel components, an increased capacity to contain added insoluble solids while having sufficient internal matrix strength to maintain individual dose units, which are capable of being molded and delivered directly to consumers in the same receptacle.

The term "ingestible" is meant to include all materials which are used by, or which perform a function in the body. Thus, materials which are not adsorbed or absorbed are included as well as non-digestible and digestible materials.

The term "insoluble solids" as used herein means those materials which, when added to the pectin-algin gel system, remain insoluble during preparation and storage, but which are released and may be solubilized during mastication and ingestion. Useful materials include celluloses; seeds such as flax, sesame and locust bean seeds; seed husks such as psyllium; cereal brans such as oat, wheat, corn, rye, barley; legumes such as guar, pea, soybean; drugs; fruit in the form of pulp, flakes, powder, and the like, and mixtures thereof.

The term "sugarless" is meant to include all hydrogenated starch hydrolysates comprising polyol blends of sorbitol and its oligomers including, maltitol, maltotriitol, maltotetratol and maltohexatol, and other hydrogenated polysaccharides and the like, singelly or in combination, and specifically including such commercially available hydrogenated starch hydrolysate mixtures as Lycasine ® and Hystare ®, intended for use as sugarless bulking agents.

The term "drug" includes medicaments, vitamins, mineral supplements and other chemical or biological substances intended for use in the treatment, prevention, diagnosis, cure or mitigation of disease or illness, or substances which affect the structure or function of the body. Suitable categories of drugs that may be employed in the present delivery system may vary widely and generally represent any stable drug combination but specifically excluding calcium or calcium-containing mixtures. Illustrative categories and specific examples include:

(a) antitussives, such as dextromethorphan, dextromethorphan hydrobromide, noscapine, carbetapentane citrate, and chlophedianol hydrochloride;
(b) antihistamines, such as chloropheniramine maleate, phenindamine tartrate, pyrilamine maleate, doxylamine succinate, and phenyltoloxamine citrate;
(c) decongestants, such as phenylephrine hydrochloride, phenylpropanolamine hydrochloride, pseudoephedrine, and hydrochloride ephedrine;
(d) various alkaloids, such as codeine phosphate, codeine sulfate, and morphine;
(e) mineral supplements such as potassium chloride, magnesium oxide and other alkali metal and alkaline earth metal salts;
(f) laxatives, vitamins, and antacids;
(g) ion exchange resins such as cholestyramine;
(h) anti-cholesterolemic and anti-lipid agents;
(i) antiarrhythmics such as N-acetyl-procainamide;
(j) antipyretics and analgesics such as acetaminophen, aspirin, and ibuprofen;
(k) appetite suppressants such as phenylpropanolamine hydrochloride or caffeine; and
(l) expectorants such as guaifenesin.

Additional useful active medicaments include anti-inflammatory substances, coronary dilators, cerebral dilators, peripheral vasodilators, anti-infectives, psychotropics, antimanics, stimulants, gastro-intestinal sedatives, antidiarrheal preparations, anti-anginal drugs, vasodilators, anti-hypertensive drugs, vasoconstrictors and migraine treatments, antibiotics, tranquilizers, antipsychotics, antitumor drugs, anticoagulants and antithrombotic drugs, hypnotics, sedatives, anti-emetics, anti-nauseants, anticonsulvants, neuromuscular drugs, hyper- and hypoglycaemic agents, thyroid and antithyroid preparations, diuretics, antispasmodics, uterine relaxants, nutritional additives, antiobesity drugs, anabolic drugs, erythropoietic drugs, antiasthmatics, expectorants, cough suppresants, mucolytics, anti-uricemic drugs and the like. Mixtures of the drugs and medicaments may also be used.

The preferred drugs are laxatives, such as phenolphthalein, sennosides and danthron. Laxatives can be included in an amount of from about 1.0% to about 5.0%, and preferably from about 2% to about 3% by weight of the final delivery system. The recommended adult dosages of phenolphthalein, sennosides and danthron are known to one having ordinary skill in the art.

Cholestyramine is also a desirable active ingredient. Cholestyramine is the chloride salt of a basic anion exchange resin which has an affinity for sodium chloride and a particularly strong affinity for acid materials such as bile acids. It occurs as an off-white powder, insoluble in water and has an amine-like odor and a gritty taste. Cholestyramine is believed to absorb and combine with bile acids in the intestine to form an insoluble complex which is then excreted by the body. Cholesterol is the major precursor of bile acids which are formed by the oxidation of cholesterol. The serum level of cholesterol can be reduced by administration of cholestyramine, which leads to reduction of bile acids and increased oxidation of cholesterol. The recommended adult dosage of cholestyramine is about 5 to about 50 grams per day; preferably about 13 to about 32 grams per day. Administration is generally about 3 to 4 times daily in dosages of about 2 to 12 and preferably about 3 to 4 grams.

The drug component can be included in the final delivery system in pharmaceutically effective amounts up to about 20% by weight.

A suitable sugarless confectionery pectin-algin gel delivery system in accordance with the present invention can be prepared by using the following formulation:

TABLE I

| Ingredient | % by weight |
| --- | --- |
| Pectin | 1% to about 5% |
| Algin | 0.2% to about 1.5% |
| Water* | 40% to about 75% |
| Acidulent/Buffer | Not more than about 5% |
| Hydrogenated Starch Hydrolysate (solids basis) | 40% to about 85% |
| Insoluble Solids | 0.5% to about 20%, |
| Humectant | 0 to about 20% |
| Polymer Gel | 0 to about 5% |
| Flavor/Colorant | 0 to about 2% |

The gel base is prepared by first dryblending the pectin and algin. This blend is then dispersed in the water to cause hydration and mixed until lump-free. The pH is maintained below about 4.5 with the acidulent/buffer. Hydrogenated starch hydrolysate (HSH) is then added and mixed until uniform. Up to this point, the process can be conducted at room temperature. The mixture is then boiled to obtain a desired solids content level, e.g., typically about 80 to about 90%, preferably about 81 to about 88%. The pH is again adjusted by adding a solution of acid, e.g., citric acid, to bring the pH into the gelling range of the pectin-algin system. It should be mentioned that the water content of the final gel, about 12% to 20%, is lower than the initial water content due to evaporation.

A second mixture can then be prepared by hydrating the insoluble solids, such as dehydrated fruit, along with any other components which are to be included. These components can include humectant(s), gelatin and flavor/colorant components. The humectant can be glycerin, propylene glycol or other similar substance having an affinity for water with a stabilizing action on the water content of a material. The second mixture is added to the first mixture while the first mixture is still hot, e.g., at a temperature about 100° C. Mixing is continued until uniformity is achieved. Finally, a drug component can be mixed in. Because the active ingredient can be added at the end of the processing cycle, potential thermal deterioration of that active is thereby minimized.

Furthermore, the addition of gelatin, or glycerin and gelatin can increase the working time of the delivery system prior to gelation. The characteristics of a combination valence-polymer network gel permits the inclusion of more solids into the delivery system than allowed with a pure pectin gel system. The film-forming properties of gelatin polymer act synergistically with the valence gel network of the pectin and the algin.

Normally, the pectin-algin gel would then have to be poured into starch molds, requiring tedious effort to form a unit dose, clean the product and regenerate the starch mold after removal of the product. In order to avoid conventional starch molding, additional cooking is usually required to obtain the correct solids content. This additional cooking, however, results in a product which is too viscous to pour, and which, upon solidification, is a tough, rubbery textured product.

Conversely, in the present delivery system, the pectin-algin gel will gel without stoving. Additionally, it can be poured directly into a receptacle such as a plastic or aluminum blister receptacle, as opposed to conventional starch molds. The composition will gel in the blister receptacle to form a structurally coherent unit which can be dispensed intact from the blister by deformation of the blister well without sticking to the surface of the well. Thus, the blister serves as both the mold as well as the final commercial container or package per se.

Thus, the problems associated with the direct replacement of sucrose/corn syrup sweetener disclosed in the prior art with hydrogenated starch hydrolysates, i.e., significantly increased water activity, increased depositing viscosity, and a tough-textured and sticky product, have been overcome and a sugarless pectin-like gel delivery system has been formulated. Surprisingly, the addition of about 0.2% to about 1.5% by weight algin to the pectin allows for the production of a suitable sugarless confectionery gel delivery system. The use of, for example, Lycasine ® or Hystar ® in place of the sucrose/corn starch syrup sweetener set forth in U.S. application Ser. No. 032,840 discussed above, produced a very sticky product with a significantly high water activity which resulted in a deleterious effect on the microbial stability of the product. Removal of some of the moisture caused an increase in the depositing viscosity beyond the acceptable range and rendered the product very difficult and, in fact, nearly impossible, to handle. The product so formed had a very tough and rubbery, unpalatable texture. Surprisingly, the pectin-algin based gel system, together with hydrogenated starch hydrolysates, yielded a product with the desired tenderness of a pure pectin gel system, with the acceptable working qualities of a pure pectin gel system, but, without the use of a sucrose/corn syrup sweetener or the like. Thus, this invention makes available a sugarless pectin-algin confectionery gel delivery system heretobefore unavailable.

Thus, where the soft, tender-textured pectin gel matrices have normally been used, for example, in centers of chocolate-covered jellies, etc., now a single soft-textured sugarless combination pectin-algin confectionery unit, having its own structural integrity, can be provided. Moreover, due to the primarily non-reversible nature of such pectin-algin gels, once set, the gel will not generally be capable of resetting into its original form. Thus, this product is suited for commercial distribution in the same mold in which it was manufactured, because tampering could be detected by evidence of product degradation or deformation.

The sweeteners used in the present delivery system can be sugarless sweeteners including but not limited to hydrogenated starch hydrolysates, sugar alcohols, and mixtures thereof. Artificial sweeteners can also be used, such as saccharin acid and its salts, cyclamic acid and its salts, acesulfame salts, dipeptide based sweeteners, talin, monellin, dihydrochalcone and chlorinated sugars including 1,6-dichloro-1,6-dideoxy-beta-D-fructofuranosyl-4-chloro-4-deoxy-alpha-D-galachopyranoside and mixtures thereof. The present inventors have unexpectedly discovered that the use of sugarless hydrogenated starch hydrolysates in combination with the present pectin-algin gel system permits a texture comparable to sucrose pectin gels.

An especially effective formulation for the present delivery system is set forth below.

TABLE II

| Ingredient | % by Weight |
| --- | --- |
| Pectin | 1% to about 3% |
| Algin | 0.5% to about 1.0% |
| Water | 12% to about 20% |
| Acidulent/Buffer | 1.2% to about 3.5% |
| Hydrogenated Starch Hydrolysate (solids basis) | 50% to about 75% |
| Dehydrated Fruit | 4.0% to about 11% |
| Glycerin | 0% to about 20% |
| Gelatin | 0% to about 3% |
| Flavor/Colorant | 0% to about 2% |

Upon chewing, the short-texture and lubricity of the masticated particles permit the pectin-algin delivery systems to be easily swallowed. The system's, texture helps to minimize the contact between the mouth taste sensor and potentially unpalatable active ingredients, and, unlike certain other gels such as calcium alginate or xanthan gum-locust bean gum, combination pectin-algin gels dissolve completely in an aqueous environment to assure release of the active ingredient. Thus, the unit dosage form is easy to chew which makes it especially desirable for geriatric use. Moreover, combination pectin-algin gels deliver a degree of satiety when consumed, and such gels also have acknowledged desirable physiological properties such as blood sugar moderation.

The following examples serve to provide further appreciation of the invention but are not meant in any way to restrict the effective scope of the invention. All percentages throughout the specification are by weight percent of the final delivery system unless otherwise indicated.

EXAMPLE 1

COMPARATIVE A

About 4.375 grams of citric acid, 4.46 grams of sodium citrate, 11.815 grams standard 150 grade slow-set pectin and 4.0 grams sodium alginate were dryblended. This blend was then dispersed in about 225 grams of water and mixed until lump-free. To this added 490 grams hydrogenated starch hydrolysate (367.5 grams solids). This first mixture was boiled to achieve about 85.5% solids.

A second mixture was prepared by combining 18.0 grams dehydrated apples, 8.0 grams dehydrated cranberries and 3.5 grams citric acid with a solution of 10.0 grams 140 bloom gelatin hydrated with 27.97 grams of water. The first and second mixtures were blended until the two became uniformly dispersed in each other.

The resulting gel formulation was deposited into blister molds holding about 3.5 grams of gel. The resulting gel formulation was found to be too thick to deposit and, after cooling, the texture of the final product was very tough and rubbery. The product surface appearance was found to be very unattractive.

EXAMPLE 2

COMPARATIVE B

About 4.375 grams of citric acid, 4.46 grams of sodium citrate, 8.86 grams standard 150 grade slow-set pectin and 4.0 grams sodium alginate were dryblended. This blend was then dispersed in about 225 grams of water and mixed until lump-free. To this added 490 grams hydrogenated starch hydrolysate (367.5 grams solids). This first mixture was boiled to achieve about 85.5% solids.

A second mixture was prepared by stirring 18.0 grams dehydrated applies, 8.0 grams dehydrated cranberries and 3.5 grams citric acid into 27.97 grams of water. The first and second mixtures were blended until the two became uniformly dispersed in each other.

The resulting gel formulation was deposited into blister molds holding about 3.5 grams of gel. This gel formulation easily approached that of a sugar pectin gel, however, resulting texture of the product was very moist, sticky and tacky.

EXAMPLE 3
COMPARATIVE C

About 4.375 grams of citric acid, 4.46 grams of sodium citrate, 11.815 grams standard 150 grade slow-set pectin and 4.0 grams hydroxypropyl methylcellulose (methocel E50LV) were dryblended. This blend was then dispersed in about 225 grams of water and mixture until lump-free. To this was added 490 grams hydrogenated starch hydrolysate (367.5 grams solids). This first mixture was boiled to achieve about 85.5% solids.

A second mixture was prepared by combining 18.0 grams dehydrated apples, 8.0 grams dehydrated cranberries and 3.5 grams citric acid with a solution of 10.0 grams 140 bloom gelatin hydrated with 27.97 grams of water. The first and second mixtures were blended until the two became uniformly dispersed in each other.

The resulting gel formulation was deposited into blister molds holding about 3.5 grams of gel. The gel formulation deposited very easily, however the mold release was unsatisfactory. The final product piece texture crumbled easily under the strain of demolding and handling.

EXAMPLE 4
INVENTIVE 1

About 4.375 grams of citric acid, 4.46 grams of sodium citrate, 8.86 grams standard 150 grade slow-set pectin and 4.0 grams sodium alginate were dryblended. This blend was then dispersed in about 225 grams of water and mixed until lump-free. To this was added 490 grams hydrogenated starch hydrolysate (367.5 grams solids). This first mixture was boiled to achieve 85.5% solids.

A second mixture was prepared by combining 18.0 grams dehydrated apples, 8.0 grams dihydrated cranberries and 3.5 grams citric acid with a solution of 5.0 grams 140 bloom gelatin hydrated with 27.97 grams of water. The first and second mixtures were blended until the two became uniformly dispersed in each other.

The resulting gel formulation was deposited into blister molds holding about 3.5 grams of gel. The gel formulation deposited easily, comparable to Example 2, however, the final gel product was less moist and sticky than that produced in Example 2.

EXAMPLE 5
INVENTIVE 2

About 4.375 grams of citric acid, 4.46 grams of sodium citrate, 10.3375 grams standard 150 grade slow-set pectin and 4.0 grams sodium alginate were dryblended. This blend was then dispersed in about 225 grams of water and mixed until lump-free. To this was added 490 grams hydrogenated starch hydrolysate (367.5 grams solids). This first mixture was boiled to achieve about 85.5% solids.

A second mixture was prepared by combining 18.0 grams dehydrated apples, 8.0 grams dehydrated cranberries and 3.5 grams citric acid with a solution of 10.0 grams 140 bloom gelatin hydrated with 27.97 grams of water. To this was added 3.0 grams distilled acetylated monoglycerides (Myvace®), an anti-sticking agent. The first and second m blended until the two became uniformly dispersed in each other.

The resulting gel formulation was deposited into blister molds holding about 3.5 grams of gel. The resulting product deposited and demolded readily. The initial water activity was 0.688. The final sugarless product piece firmness as measured by Instron annulus and plunger peak force was 0.87 kgf which is comparable to that of a sugar pectin gel.

Figure 2:
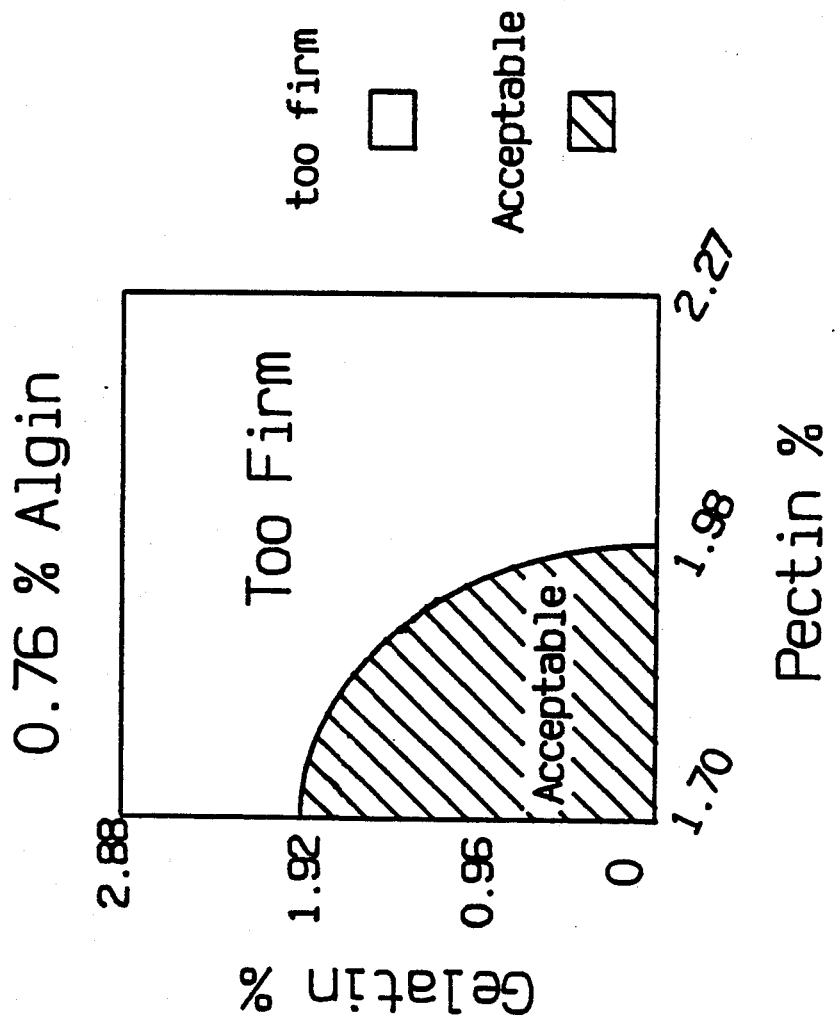
FIG. 2 depicts a slice of an inventive tri-axial graph of gel product properties using varying concentrations of pectin and gelatin with the algin concentration constant at about 0.76% by weight.
Figure 3:
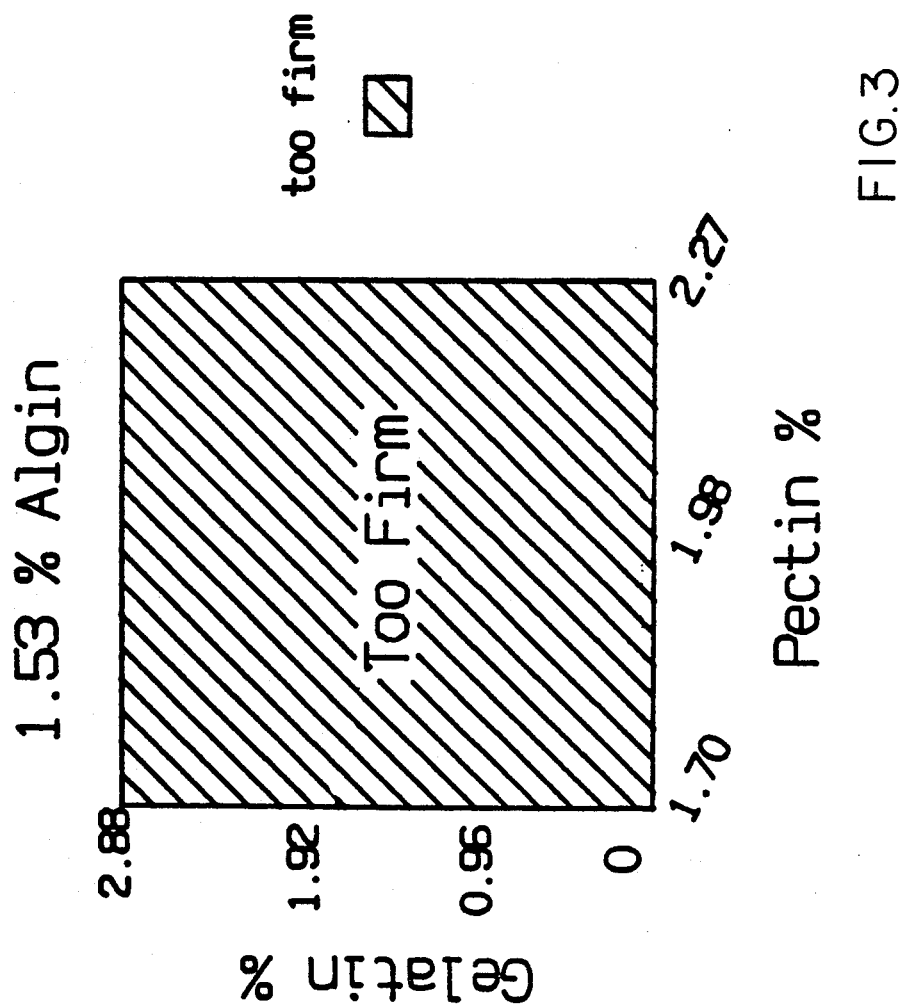
FIG. 3 depicts a slice of a comparative tri-axial graph diagram of gel product properties using varying concentrations of pectin and gelatin with the algin concentration constant at about 1.53% by weight.

Referring now to the figures, FIGS. 1, 2 and 3 are slices of a tri-axial graph describing gel characteristics as functions of pectin, gelatin and algin level. These slices are made to correspond to 0% (FIG. 1), 0.76% (FIG. 2) and 1.53% (FIG. 3) added algin. At these algin levels the effect of varying pectin and gelatin concentration is described.

Thus, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

We claim:

1. A sugarless ingestible gel confectionery delivery system comprising:
   (a) a pectin gel component in an amount of from about 1% to about 5% by weight of the final delivery system,
   (b) an algin gel component in an amount of from about 0.2% to about 1.5% by weight of the final delivery system,
   (c) a polymer network gel component in an amount of up to about 5% by weight of the final delivery system, and
   (d) an edible insoluble solid in an amount sufficient to strengthen the internal gel network such that the gel retains its structural integrity during mold removal.

2. The delivery system of claim 1 wherein said insoluble solid is selected from the group consisting of cellulose, microcrystalline cellulose, gums, grains, seeds, seed husks, fruits and mixtures thereof.

3. The delivery system of claim 2 wherein said gums include guar gum and locust bean gum.

4. The delivery system of claim 2 wherein said grains include cereal brans selected from the group consisting of corn, wheat, oats, rye, barley bran, and mixtures thereof.

5. The delivery system of claim 2 wherein said fruits are dehydrated apples and cranberries.

6. The delivery system of claim 2 wherein said seed husk is selected from the group consisting of psyllium seed husk, psyllium seed coating and psyllium hydrophilic mucilloid.

7. The delivery system of claim 1 wherein said polymer network gel forming agent is gelatin included in an amount of from about 0 to about 5% by weight of the final delivery system.

8. The delivery system of claim 1 which further incorporates a humectant.

9. The delivery system of claim 8 wherein said humectant is glycerin added in an amount of from about 0 to about 20% by weight of the final delivery system.

10. The delivery system of claim 1 wherein said amount of pectin is from about 1.0% to about 3.0% by weight of the final delivery system.

11. The delivery system of claim 1 wherein said amount of algin is from about 0.5% to about 1.0% by weight of the final delivery system.

12. The delivery system of claim 1 wherein said insoluble solid is included in an amount of from about 0.5% to about 20.0% by weight of the final system.

13. The delivery system of claim 12 wherein said amount of insoluble solid is from about 4.0% to about 10.0%.

14. The delivery system of claim 1 which further comprises a sugarless hydrogenated starch hydrolysate, a drug ingredient, an acidulent/buffer ingredient, water, humectants, and flavor/colorant agents.

15. The delivery system of claim 14 wherein said delivery system has the following formulation:

| Ingredient | % by Weight |
| --- | --- |
| Pectin | 1% to about 5% |
| Algin | 0.2% to about 1.5% |
| Water | 12% to about 20% |
| Acidulent/Buffer | Not more than about 5% |
| Hydrogenated Starch Hydrolysate (solids basis) | 40% to about 85% |
| Insoluble Solids | 0.5% to about 20% |
| Humectant | Not more than about 20% |
| Gelatin | Not more than about 5% |
| Flavor/Colorant | Not more than about 2% |

16. The delivery system of claim 15 wherein said formulation is as follows:

| Ingredient | % by Weight |
| --- | --- |
| Pectin | 1% to about 3% |
| Algin | 0.5% to about 1.0% |
| Water | 12% to about 20% |
| Acidulent/Buffer | 1.2% to about 3.5% |
| Hydrogenated Starch Hydrolysate (solids basis) | 50% to about 75% |
| Dehydrated Fruit | 4.0% to about 12% |
| Glycerin | Not more than about 20% |
| Gelatin | Not more than about 3% |
| Flavor/Colorant | Nor more than about 2% |

17. The delivery system of claim 1 which further comprises a drug in a unit dosage amount.

18. The delivery system of claim 17 wherein said drug is a laxative included in an amount of from about 0.4% to about 2.5% by weight of the final delivery system.

19. The delivery system of claim 18 wherein said amount of laxative is from about 1.0% to about 2.0% by weight of the final delivery system.

20. The delivery system of claim 14 wherein said sugarless hydrogenated starch hydrolysate is a polyol blend of sorbitol and its oligomers including maltitol, maltotriitol, maltotetratol, maltohexatol and other hydrogenated polysaccharides, and mixtures and combinations thereof.

21. The delivery system of claim 20 wherein there is additionally added a sweetener selected from the group consisting of saccharin acid and its salts, cyclamic acid and its salts, acesulfame salts, dipeptide based sweeteners, talin, monellin, dihydrochalcone and chlorinated sugars including 1,6-dichloro-1,6-dideoxy-beta-D-fructofuranosyl-4-chloro-4-deoxy-alpha-D-galachopyranoside and mixtures thereof.

22. The delivery system of claim 1 which further comprises a nutritional supplement and/or a drug or medicament and mixtures thereof.

23. The delivery system of claim 22 wherein said drug is a laxative.

24. The delivery system of claim 23 wherein said laxative is selected from the group consisting of phenolphthalein, sennosides and danthron.

25. A method of providing a sugarless ingestible gel delivery system product formed during processing as a confectionery unit in a mold receptacle and capable of being dispensed directly from said receptacle by a consumer, comprising:
(a) forming a combination pectin-algin gel composition having a pectin gel component in an amount of from about 1% to about 5% by weight, an algin gel component in an amount of from about 0.2% to about 1.5% by weight and a polymer network gel component in an amount of up to about 5% by weight and having sufficient insoluble solids to strengthen the internal gel network and to absorb internal moisture sufficient to reduce the adhesive nature of said product thereby enhancing its removability from said mold receptacle,
(b) depositing said composition into said mold receptacle, and
(c) allowing said composition to gel to said product.

26. The method of claim 25 wherein said molds are plastic or aluminum blister receptacles.

27. The method of claim 25 wherein said amount of pectin is from about 1.0% to about 3.0% by weight of the final delivery system.

28. The method of claim 25 wherein the amount of algin is from about 0.5% to about 1.0% by weight of the final delivery system.

29. The method of claim 25 wherein said insoluble solids are added in an amount of about 0.5% to about 20% by weight of the final delivery system.

30. The method of claim 29 wherein said amount of insoluble solids is from about 4.0% to about 10.0% by weight of the final delivery system.

31. The method of claim 25 wherein the time of gelation is controlled by use of buffer/acidulent and insoluble solids components.

32. The method of claim 25 wherein the time of gelation is controlled by the ratio of pectin to algin.

33. The method of claim 25 wherein the time of gelation is controlled by the ratio of pectin to algin to polymer network gel former.

34. The method of claim 25 wherein the amount of insoluble solids added is increased by use of polymer network gels and humectants.

35. The method of claim 25 wherein the amount of insoluble solids added is increased by use of pectin-aglin blends.

36. The method of claim 34 wherein said polymer network gel is gelatin and said humectant is glycerin.

37. A sugarless confectionery dosage unit comprising a combination pectin-algin delivery system having a pectin gel component, an algin gel component and a polymer network of gel component in amounts sufficient to form a gel confectionery unit and an edible insoluble solid in an amount sufficient to strengthen the internal gel network such that the gel retains its structural integrity.

* * * * *